United States Patent [19]

Crespi

[11] Patent Number: 5,128,255

[45] Date of Patent: Jul. 7, 1992

[54] METHOD AND A PREPARATION TO SELECT FOR TRANSFECTED DNA IN MAMMALIAN CELLS

[75] Inventor: Charles L. Crespi, Marblehead, Mass.

[73] Assignee: Gentest Corporation, Woburn, Mass.

[21] Appl. No.: 280,742

[22] Filed: Dec. 6, 1988

[51] Int. Cl.$^5$ .................. C12N 5/00; C12N 15/00; C12Q 1/04; C12Q 1/24

[52] U.S. Cl. .................. 435/172.3; 435/30; 435/34; 435/172.1; 435/240.2; 435/320.1; 935/55; 935/66

[58] Field of Search ............ 435/172.3, 240.2, 6, 435/34, 320.1, 172.1, 30; 935/55, 56, 57, 58, 66, 69, 72, 22-32, 70, 71, 79, 84

[56] References Cited

FOREIGN PATENT DOCUMENTS 0054223 6/1982 European Pat. Off. .

OTHER PUBLICATIONS

Jouanneau et al. 1985, Eur. J. Biochem. 146(1) pp. 173–178.

Lehninger, 1975, Biochemistry, Worth Publishers, Inc. Hartman, S. C. and Mulligan R. C., "Two Dominant-Acting Selectable Markers for Gene Transfer Studies in Mammalian Cells", Proc. Natl. Acad. Sci. USA, vol. 85, pp. 8047–8051, Nov., 1988.

*Primary Examiner*—David L. Lacey
*Assistant Examiner*—Gian Wang
*Attorney, Agent, or Firm*—Wolf, Greenfield & Sacks

[57] ABSTRACT

The invention provides methods and products equal in a selection system for determining the presence or absence of a vector in a mammlian cell. The vector of the invention carries and is capable of expressing a gene encoding a protein capable of effecting the conversion of a precursor to an essential amino acid. A mammalian cell line is created with conditions capable of causing the vector to be introduced into the mammalian cell line. Then, the created mammalian cell line is grown in medium containing a precursors to the essential amino acid but not containing the growth-supporting amount of the essential amino acid and those cells capable of growing are selected.

7 Claims, 2 Drawing Sheets

METHOD AND A PREPARATION TO SELECT FOR TRANSFECTED DNA IN MAMMALIAN CELLS

TECHNICAL FIELD

This invention generally relates to the fields of molecular biology and biochemistry and more specifically relates to methods and products useful in determining whether a vector has been introduced into a mammalian cell line.

BACKGROUND OF THE INVENTION

The ability to introduce foreign genes into mammalian cells has proven to be a powerful tool both in the research laboratory and for the commercial production of biologicals. Foreign genes are commonly introduced either on plasmid or viral vectors or by co transfection with such vectors. Several different methods have been used to introduce foreign genes including calcium phosphate precipitation, protoplast fusion, electroporation and viral infection. For many combinations of vectors, transfection methods, and mammalian cell lines, stable transfection is a rare event. Methods for the selection of cells containing foreign DNA are usually necessary. Therefore, selectable markers have been incorporated into many vectors.

There are a number of different selective methods for transfected DNA in mammalian cells. These methods may be divided into two classes based on the conferred phenotype. The first class consists of selection relating to dominant drug resistant markers. Markers in this class include resistance to neomycin (G418) (Southern and Berg, 1982), hygromycin B (Sugden et al., 1985) and mycophenolic acid (Mulligan and Berg, 1985). The second class consists of selection relating to complementation of an auxotrophic mutation. Several examples of this approach include the thymidine kinase (tk) gene (Wigler et al., 1977), the hypoxanthine guanine phosphoribosyl transferase (hgprt) gene (Mulligan and Berg, 1985) and the dihydrofolate reductase gene (dhfr) (Kaufman and Sharp, 1982).

The selective systems mentioned above have found broad applicability to the introduction of foreign DNA into a variety of mammalian cell types. However, there are limitations to each of the individual approaches. For example, some cell lines are natively resistant to G418: others grow poorly in mycophenolic acid even in the presence of the vector; and still others have a reduced growth rate under hygromycin B selection. Selection methods using neomycin and hygromycin B require high concentrations (greater than 100 ug/ml) and therefore are relatively expensive. Hygromycin B is also unstable in cell culture medium necessitating frequent refeeding in order to maintain selection.

Selection methods relying upon the complementation of auxotrophic mutations also have drawbacks. In contrast to dominant marker systems, further modification to the recipient cell is required. These systems also require the isolation of rare tk deficient, hgprt deficient or dhfr deficient cells This limits these approaches to cell lines where such mutants already exist or cell lines with high cloning efficiencies such that appropriate mutants may be isolated.

Aside from the drawbacks of known selective systems, it is sometimes necessary to independently introduce several different genes into a single cell line. Therefore, it is desirable to have several independent selective systems.

A new selective approach should have the following properties. Preferably, the selective marker is not normally present in the recipient cell line. Therefore, the recipient cell line does not have to be modified by, for example, mutation to remove a native property, and the usefulness of the marker does not depend upon the ability to create such a mutation. Most preferably the selective marker is not present in mammalian cells so that the selective system may be used in connection with mammalian cells. Further, the gene encoding the selective marker preferably is relatively small in order to facilitate introduction into vectors with limited "available space." The products used in the selective system should be stable in cell culture medium. Finally, the products used in the selective system should be relatively inexpensive. These and other objects are achieved according to the invention.

SUMMARY OF THE INVENTION

The invention relates to a method for selecting for a vector introduced into mammalian cells. Mammals are not capable of synthesizing some amino acids which are referred to as essential amino acids. Because they cannot synthesize the essential amino acids, mammalian cells in culture will not grow unless these amino acids are supplied in the growth medium. However, other organisms such as bacteria are capable of synthesizing these amino acids from a suitable precursor(s). According to the invention, a non-mammalian gene(s) which encodes an enzyme(s) involved in the non-mammalian biosynthesis of an essential amino acid is incorporated into a vector. This gene(s) is incorporated into the vector in such a way that it can be expressed when the vector is introduced into a host mammalian cell.

Thus, the invention provides a method for selecting for mammalian cells containing a vector. First, the vector is provided. The vector carries and is capable of expressing in mammalian cells a gene, the expression of which gene results in a protein capable of effecting the conversion of the precursor to an essential amino acid. The mammalian cell line then is treated with conditions capable of causing the vector to be introduced into the mammalian cell line. Then, the cells containing the vector are selected by growing the treated cells in the absence of a growth-supporting, exogenous supply of the essential amino acid but in the presence of the precursor. Only those cells containing the vector will be capable of growing under such conditions.

Preferably, the gene product is an enzyme and the treated cells are grown in medium containing a precursor to the essential amino acid, but not containing a growth supporting amount of the essential amino acid. In this manner, the expression of the gene carried on the vector will result in the production of an enzyme which will convert the precursor into the essential amino acid thereby allowing the cells to grow. Preferably the precursor is selected from the group consisting of α-keto β-methyl valeric acid, α-ketoisocaproic acid, meso-α,ε-diaminopimelic acid, saccharopine, homocystene, cystathionine, phenylpyruvic acid, homoserine phosphate, homoserine, indole-3-glycerol phosphate, α-ketovaleric acid and histidinol.

Preferably, the vector is carrying and capable of expressing a gene encoding an enzyme involved in the synthesis of an amino acid selected from the group consisting of arginine, histidine, isoleucine, leucine, lysine, methionine, phenylalanine. threonine, tryptophan and valine. Preferably the enzyme is selected from the group consisting of α-keto-β-methyl valeric acid transaminase, α-ketoisocaproic acid transaminase, meso-α,ε-diaminopimelic acid decarboxylase, phenylpyruvic acid transaminase, α-ketoisovaleric acid transaminase, threonine synthetase, tryptophan synthetase and histidinol dehydrogenase.

Most preferably, the vector contains the *E. coli* histidinol dehydrogenase (HDH) gene. In *E. coli* and other micro organisms, the enzyme HDH catalyzes the final step in the biosynthesis of histidine, the conversion of histidinol to histidine. Histidine is an essential amino acid for mammalian cells. In the preferred vector, the bacterial HDH gene is promoted by the Herpes Simplex Virus (HSV) thymidine kinase (tk) gene promoter and is joined to the HSV tk 3' polyadenylation signal which allows the expression of the HDH gene in mammalian cells. When the host mammalian cells are transfected with the vector, cells which take up and express the vector DNA can be selected for by growth in culture medium which does not contain the essential amino acid but does contain the suitable precursor of the essential amino acid. Only those cells containing the vector and expressing the HDH gene will grow.

An example of the selection medium of the invention is a medium essentially equivalent to RPMI 1640, but containing histidinol instead of histidine.

The invention also provides a mammalian cell or mammalian cell line transfected with the vector of the invention.

These and other aspects of the invention will be better understood with reference to the drawings and to a particular example.

DETAILED DESCRIPTION OF A PREFERRED EMBODIMENT

Figure 1:
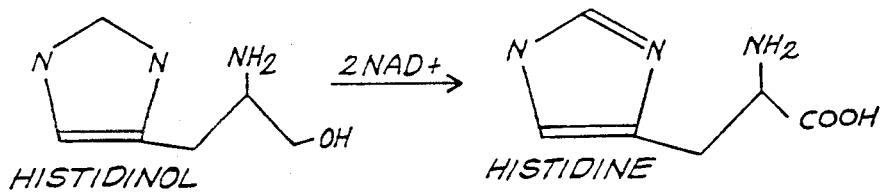
FIG. 1 depicts the reaction catalyzed by histidinol dehydrogenase.

The following embodiment of the invention is based on the histidinol dehydrogenase (HDH) gene and its ability to confer growth in medium containing histidinol, but not containing histidine. HDH catalyzes the final step in the biosynthesis of histidine in bacterial cells and other micro-organisms. The reaction catalyzed by HDH is diagrammed in FIG. 1. Histidine is an essential amino acid for mammalian cells and this nutritional requirement is typically supplied by the cell culture media. HDH activity is not present in mammalian cells.

According to the invention, a vector expressing HDH when introduced into mammalian cells allows mammalian cells to metabolize histidinol to histidine. This provides a basis for selection of transfectants if the medium contains histidinol and is substantially free of histidine. In addition, histidinol is a reversible inhibitor of protein synthesis in human cells (Hansen et al., 1972) in the absence of substantial amounts of histidine. This inhibition by histidinol of protein synthesis still is present even in the presence of low levels of histidine (present by way of the serum, for example). The mechanism of inhibition of protein synthesis appears to be mediated through histidinol substitution for histidine on the tRNA which then blocks protein elongation. Thus, according to the invention, two levels of selection are provided. First, the provision of the histidine required to support cell growth and second, the removal of the inhibitory histidinol from the medium.

HDH functions as a multimer with identical subunits (Burger et al., 1979). The apparent molecular weight of the active species in *S. typhimurium* is 83,000 daltons. The HDH gene has been cloned from *E. coli* and the nucleotide sequence has been reported (Bruni et al., 1980; Chiariotti et al, 1986). The HDH gene contains 1,305 base pairs and encodes a protein with an approximate molecular mass of 22,700 daltons. The HDH gene is sufficiently small to allow for its incorporation into many vector systems. For comparison purposes, the genes which confer resistance to neomycin or hygromycin B are each approximately 1000 bp.

MATERIALS AND GENERAL PROCEDURES

Materials

Restriction endonucleases were obtained from New England Biolabs, Beverly Mass. and were used according to the manufacturer's recommendations. Horse serum was obtained from Hazelton Inc., Denver, Pa. Hygromycin B was obtained from Calbiochem, LaJolla, Calif. Luria broth contains 10gm/l Bacto-tryptone, 5gm/l Bacto yeast extract, and 10gm/l NaCl and was obtained from Difco Laboratories, Detroit, Mich. All other medium, medium components and chemicals were obtained from Sigma Chemical Company, St. Louis, Mo. The L3 human lymphoblastoid cell line is a derivative of the AHH-1 cell line (Crespi and Thilly, 1984). The AHH-1 cell line may be substituted for L3 cells in the procedures outlined herein. AHH-1 is available from the ATCC, Rockville, Md., USA under accession No. CRL 8146. Further, the selection system described herein is intended for use in all mammalian cell lines and the invention is not limited to the particular cell line used in the example described below. Recombinant DNA procedures were performed according to standard techniques (Maniatis et al, 1982).

Isolation of the Histidinol Dehydrogenase Gene.

We have isolated a portion of the histidine operon from the standard *E. coli* strain HB 101. HB 101 is commercially available from Bethesda Research Lab., Gaithersburg, Md. Our isolation was based on the published restriction map for this operon. The HDH gene is contained with a 5.3 kb Hind III fragment of genomic DNA. *E. coli* DNA was digested with Hind III, fractionated based on molecular weight and fragments of 5.3 kb were isolated. The 5.3 kb fragments were introduced into the unique Hind III site of pUC19 a plasmid commercially available from Bethesda Research Laboratories, Gaithersburg, Md. Forty-five recombinant plasmids were screened for restriction sites characteristic of the desired fragment. Each plasmid was first screened for Pst I restrictions sites. Promising candidate plasmids were then screened for Bgl II and Hpa I restriction sites. One isolate designated pHis17 was found to have a restriction map identical to that reported in the literature (Chiariotti et al, 1986). A restriction map of our isolate pHIS17, along with the published restriction map reported in the literature, is presented in FIG. 2. Data for Ava II sites are available for pHis17 only. The pUC19 DNA of the pHis17 isolate is not shown.

Introduction of the Histidinol Dehydrogenase Gene into a Vector.

The next step was the introduction of the HDH gene into a vector system which would allow HDH expression in mammalian cells. For this study we performed additional restriction mapping in order to identify a means for relatively efficient excision of the HDH gene from pHis17.

Figure 2:
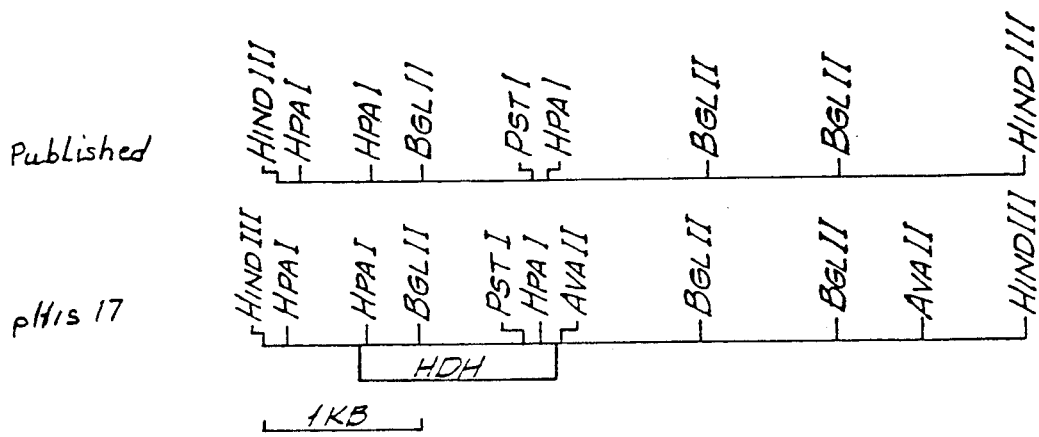
FIG. 2 depicts the published restriction map of the *E. coli* his operon fragment and the observed restriction map of the pHis17 isolate which contains substantially the same fragment.

Additional restriction mapping indicated that the enzymes Ava II and Hind III were relatively efficient at excising the HDH gene from the pHis17 isolate (FIG. 2). Ava II cut the isolate approximately 50 bp 5' to the HDH gene and Hind III cut the isolate approximately 600 bp 3' to the HDH gene. The resulting fragment was approximately 2 kb long.

The Ava II/Hind III fragment was rendered blunt ended and modified by the addition of Sal I linkers. The modified fragment was introduced into the pMF6 expression vector. The pMF6 expression vector is a modification of the pHEBo vector developed by Sugden et al, (1985). The pHEBo vector was obtained from Dr. Sugden of the University of Wisconsin, Madison, Wis. However, it will be understood by those skilled in the art that a wide variety of vectors may be substituted for this and for the other vectors employed.

The vector pHEBo bears the genes for ampicillin resistance and hygromycin resistance, and contains sequences from the origin of replication of the Epstein-Barr virus which allow it to replicate autonomously in Epstein-Barr virus-transformed lymphoblastoid cells (Sugden et al, 1985). pHEBo possesses unique sites for the enzymes Cla I, Hind III, Bam HI and Sal I, which may be used for the insertion of the DNA of interest. An expression vector derived from pHEBo and containing the HSV tk gene 5' and 3' controlling sequences flanking an unique Sal I site was constructed. Again, those skilled in the art will recognize that many other controlling sequences may be substituted.

To introduce the 3' poly A addition signal, the plasmid pHSV106 (McKnight et al, 1980a), bearing the HSV tk gene, was digested with Pvu II and Xho I linkers were added. The pHSV106 was obtained from Bethesda Research Labs, Bethesda, Md. The DNA was then digested with Sma I and Sal I linkers were attached. This resulted in a 0.6 kb fragment bearing the 3' poly A additional signals of the HSV tk (McKnight et al, 1980b; Wagner et al, 1981) which could be inserted into the Sal I site of pHEBo. pHEBo DNA was digested with Sal I and treated with alkaline phosphatase to prevent recircularization of pHEBo during the ligation reaction. Of the two possible orientations, the fragment would be correctly inserted when the preserved Sal I site at the 5' end of the fragment was proximal to the Bam HI site of pHEBo, and the nonfuctional 3' Sal I-Xho I fusion site was distal to the Bam HI site. The correct plasmid, designated p12L, was then cut with Bam HI and Sal I. HSV tk 5' promoter sequences were isolated by cutting pHSV106 with Bgl II, repairing the ends and adding Sal I linkers. The pHSV106 DNA was cut with Bam HI and the resulting 0.7 kb fragment was inserted into the Bam HI/Sal I cut p12L. The resulting plasmid, designated pMF6, bears both 5' and 3' controlling sequences from the HSV tk gene and preserved the unique Sal I site for the insertion of genes to be expressed.

Figure 3:
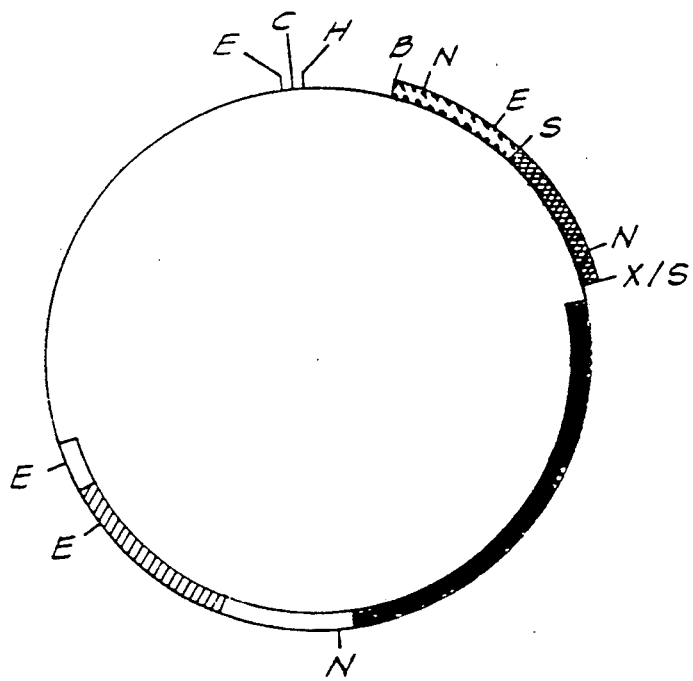
FIG. 3 is a schematic map of pMF6, a vector carrying HSV-tk derived regulatory sequences, and into which the HDH gene was introduced.

FIG. 3 is a schematic map of pMF6. The thin line represents pBR322 sequences, the black box represents EVB sequences, the open boxes are HSV-tk-derived regulatory sequences for the hyg ® gene which is the hatched box. The stippled and double hatched boxes represent the 5' and 3' sequences of the HSV-tk gene respectively. Restriction sites are indicated as follows: Bam HI, B; Cla I, C; Eco RI, E; Hind III, H; Nar I, N; Sal I, S; X/S denotes the junction formed by ligation of Xho I and Sal I ends After introduction of the HDH gene into pMF6, the orientation of the insert was verified by restriction analysis. The construct containing the HDH gene in the proper orientation was designated pAS1.

Transfection.

The plasmid pAS1 was introduced into the L3 human lymphoblast line via protoplast fusion (Yoakum et al., 1984). E. coli HB 101 containing the plasmid pAS1 were grown in Luria broth containing 50 ug/ml ampicillin (150 ml total volume). When the bacteria concentration yielded a $OD_{600}$ of 0.6, 200 ug/ml chloramphenicol was added to the culture and the culture was stirred overnight. Bacteria were centrifuged 2000×g for 10 minutes and the cell pellet resuspended in 1.5 ml of HBS-20 (20 mM HEPES, 20% sucrose, pH7.1) and 0.48 ml of a 10 mg/ml lysozyme solution (in HBS-20, filter sterilized) was added. The bacteria were incubated at room temperature for 45 minutes. The lysozyme reaction was terminated by the addition of 0.24 ml of 1.25M $CaCl_2$. Excess Ca++ was chelated by adding 0.6 ml of 0.25M EDTA. The above protoplast preparation was diluted by the addition of 6 ml of HBS-9 (20 mM HEPES, 9% sucrose, pH 7.1).

L3 cells ($2 \times 10^7$ cells) were centrifuged and the cell pellet dispersed by tapping the tube. 1.5 ml of PEG-fusion reagent (48% [w/v] polyethylene glycol purified according to Yoakum et al, [1984] with the balance RPMI medium 1640) was added to the cells. 2.5 ml of the protoplast suspension was added immediately and the resulting suspension was centrifuged at 800×g for 3 minutes. The pellet was dispersed by tapping the tube, 1.5 ml PEG-fusion reagent was added and the cells were incubated for 1 minute. The PEG-fusion reagent was diluted with 50 ml of control medium, the cells were then centrifuged and resuspended in 80 ml of control medium containing 100 U/ml Penicillin, 100 ug/ml streptomycin and 100 ug/ml gentamycin.

Selection medium.

The selection medium was a modification of RPMI 1640, lacked histidine and had the following composition (pH 6.85):

| MEDIUM COMPONENT | CONCENTRATION (mg/l) |
| --- | --- |
| Alanine | 13.35 |
| Arginine | 200 |
| Asparagine | 22.50 |
| Aspartic acid | 19.95 |
| Cystine | 50 |
| Glutamic acid | 22.05 |
| Glutamine | 300 |
| Glycine | 11.25 |
| Hydroxyproline | 20 |
| Isoleucine | 50 |
| Leucine | 40 |
| Lysine-HCl | 50 |

| MEDIUM COMPONENT | CONCENTRATION (mg/l) |
| --- | --- |
| Methionine | 15 |
| Phenylalanine | 15 |
| Proline | 17.25 |
| Serine | 15.75 |
| Threonine | 20 |
| Tryptophan | 5 |
| Tyrosine | 20 |
| Valine | 20 |
| p-Aminobenzoic acid | 1 |
| Biotin | 1 |
| Calcium pantothenate | 1 |
| Choline-HCl | 1 |
| Folic acid | 1 |
| Glucose | 3500 |
| myo-Inositol | 2 |
| Niacinamide | 1 |
| Phenol red | 5.5 |
| Pyridoxine HCl | 1 |
| Riboflavin | 0.1 |
| Thiamine | 1 |
| Vitamin $B_{12}$ | 0.005 |
| $CaCl_2$ $2H_2O$ | 132.5 |
| KCl | 200 |
| $KH_2PO_4$ | 366 |
| $MgSO_4$ | 49 |
| NaCl | 6070 |
| $NaH_2CO_3$ | 2000 |
| $Na_2HPO_4$ | 400 |
| $NaH_2PO_4$ | 61 |

Selected medium also contained varying amounts of histidinol (200–500 uM) and was supplemented with 10% horse serum. Control medium had the same formulation but contained 80 uM histidine in place of the histidinol.

EXAMPLES

Example 1

Selection by colony formation

After protoplast fusion, cells were grown for two days in control medium before beginning selection. The cultures were centrifuged to remove the histidine-containing medium. The cells were then plated in the selection medium at 20,000 cells per well in flat bottom 96 well plates (Corning, Corning, N.Y.) by the procedure of Furth et al (1981).

Histidinol resistant colonies were recovered after 14 days of incubation from the cultures treated with pAS1 at a frequency of $1 \times 10^{-6}$. No histidinol resistant cells were recovered from control cultures (less than 2633 $10^{-7}$).

Example 2

Selection in bulk culture

Figure 4:
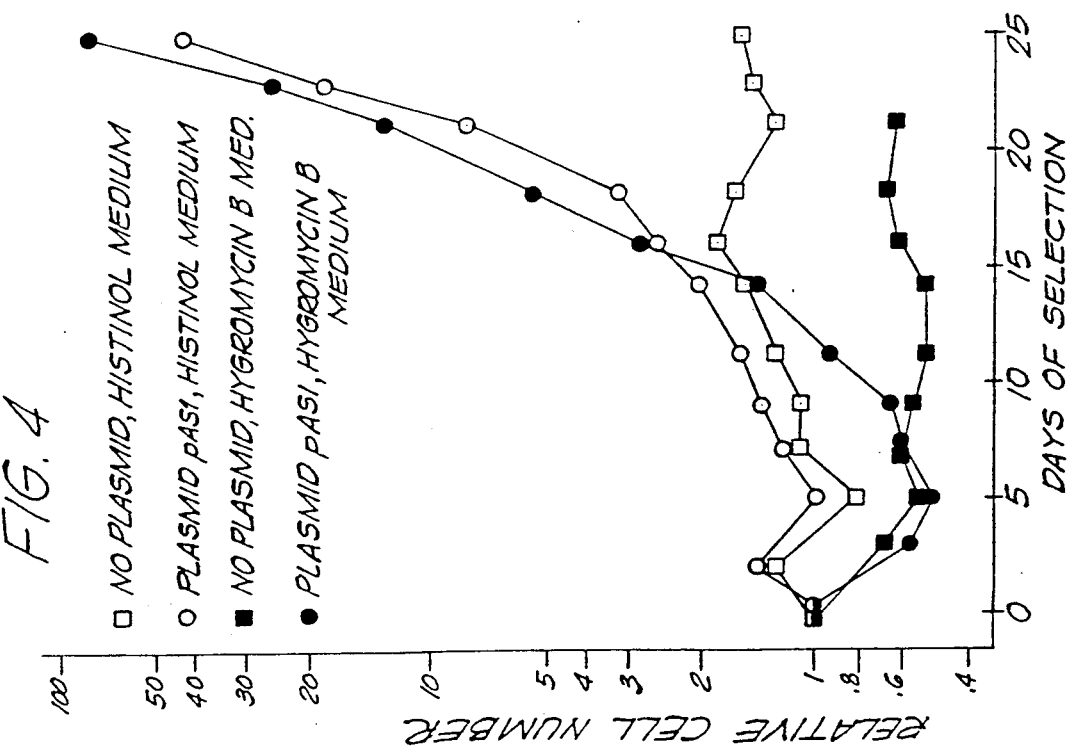
FIG. 4 depicts the growth curve of control cells and cells treated with a plasmid containing the HDH and hyg ® genes.

Selections for hygromycin resistant and histidinol-resistant bulk populations were performed concurrently with the selection for histidinol resistant cells via colony formation. The hygromycin-resistant population was selected by growth in medium containing 80 uM histidine and 400 ug/ml hygromycin B (10% horse serum). The growth curves for plasmid-treated cells and control cells without plasmid are presented in FIG. 4. The control cells did not grow appreciably in either selective media. Cells treated with plasmid showed growth in both hygromycin and histidinol after 15 days in culture. Hygromycin selection and histidinol selection appear to have comparable performance.

Example 3

Expression of unselected, co-transfected genes

Figure 5:
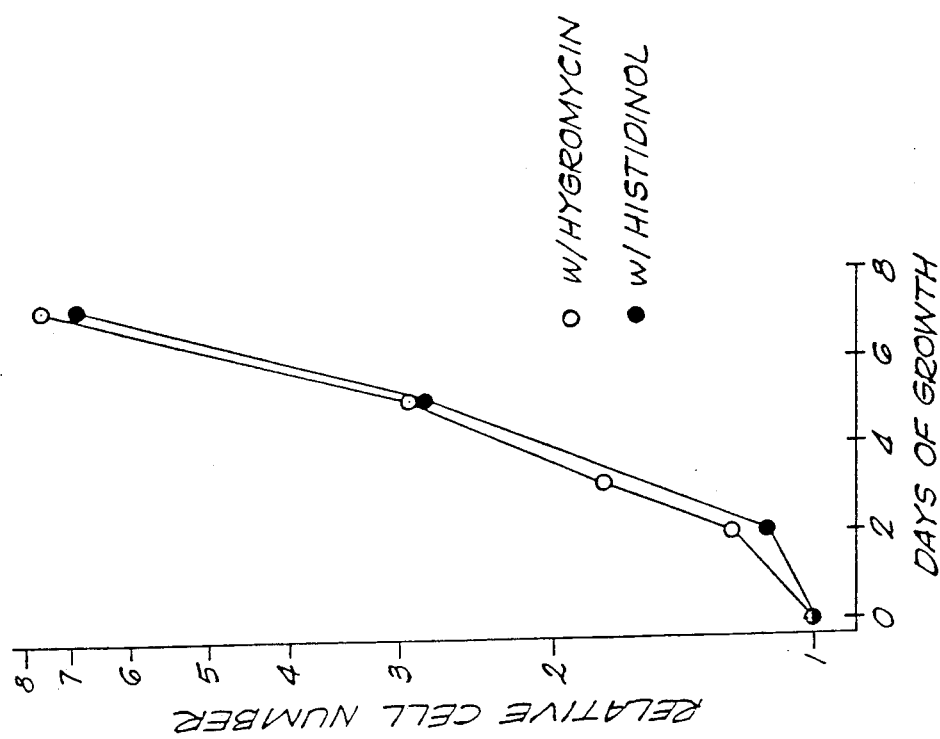
FIG. 5 depicts the growth curve of cells containing the plasmid pAS1 in medium containing hygromycin or histidinol.

Two aliquots of cells treated with plasmid pAS1 and selected for their ability to grow in medium containing histidinol were centrifuged. One was resuspended in medium containing 80 uM histidine, 200 ug/ml hygromycin B and no histidinol. The other was resuspended in medium containing 200 uM histidinol with no histidine (selection medium). As shown in FIG. 5, the growth in both cultures was equivalent.

Thus the histidinol-resistant population was completely cross resistant to hygromycin B, which was expected given that both functions are on the same plasmid. This indicates that selection of cells containing the HDH gene by growth in histidinol-containing medium can be used to select for expression of other foreign genes contained on the same vector. Those skilled in the art will recognize that the other foreign gene(s) whose expression in the host is desired, need not be on the same vector. Expression of genes which are co-transfected on a piece of DNA separate from the selectable gene can also be selected for (Wigler et al, 1979).

Those skilled in the art also will recognize many equivalents to this preferred embodiment of the invention. The gene catalyzing the last step in the biosynthesis of any essential amino acid such as tryptophan synthetase could be incorporated into the vector Selection would then be accomplished by growing the cells in medium lacking the essential amino acid but containing the precursor for the final step in the biosynthesis of the essential amino acid, such as indole-3-glycerol phosphate in the case of tyrptophan synthetase. The criteria for a successful system includes the expression of the gene, the stability of the precursor in medium and the ability of the host cell to take up the precursor from the medium. More than the final gene for the biosynthetic pathway could be included on the vector coupled with selection via growth in the presence of the appropriate intermediate precursor of the essential amino acid in place of the immediate precursor. In fact, the supplementation of the medium with a precursor of the essential amino acid is not always necessary. If, for example, the entire histidine operon were transferred, selection could be accomplished merely by growth in medium lacking histidine since mammalian cells are capable of synthesizing 5-phosphoribosyl 1 pyrophosphate which is the starting material in the biosynthesis of histidine.

It further will be understood by those skilled in the art that mutant mammalian cell lines that require for growth an amino acid normally nonessential also may be used according to the invention. In this instance, a vector carrying the gene for that enzyme capable of effecting the conversion of a precursor into that normally nonessential amino acid would be used as a selection tool. Therefore, the term "essential amino acid" may include amino acids that are not produced by the host mammalian cell line either in that particular cell line's naturally occurring condition or a mutant condition.

The preferred vector into which the HDH gene is inserted for transfection into the host cells depends on the type of host to be transfected. In the embodiment described above, a human lymphoblastoid cell line was used as the host. The pMF6 expression vector, which is a modification of the pHEBo vector developed by Sugden et al (1985), is a suitable expression vector for human lymphoblastoid cell lines. Accordingly the HDH gene was inserted into a derivative of pHEBo (pMF6) for transfection into the human lymphoblastoid cells. Other vectors, of course, are suitable for this cell line. Moreover, as is well known to those skilled in the art, other vectors would be more appropriate for other cell lines.

The preferred medium contains a precursor of an essential amino acid but does not contain a growth-supporting amount of that amino acid. The preferred selection medium for the above described embodiment is free of histidine and contains histidinol. The medium may be prepared and stored as a solution. Alternatively, the medium may be initially prepared as a powder and stored for later dissolution in a liquid such as water or physiologic saline. The preferred selection medium also depends, in part, on other characteristics of the host cells to be transfected. Human lymphoblastoid cells grow well in RPMI 1640. Thus, in the example described above, the composition of the selection medium was similar to RPMI 1640, but contained histidinol instead if histidine. Formulations based on other media such as MEM, DMEM or BME would be more appropriate, for example, for anchorage dependent cells.

LITERATURE CITED

Bruni, C. B., Musti, A. M., Frunzio R. and Blasi, F, (1980) *J. Bacterial.* 142:32.

Burger, E., Gorisch, J. and Lingens, F. (1979) *Biochem. J..* 181:771.

Chiariotti, L., Alifano, P., Carlogano, M. S. and Bruni, C. B. (1986) *Mol. Gen. Genet.*, 203:382.

Furth, E. E., Thilly, W. G., Penman, B. W., Liber, H. L. and Rand, W. G. (1981) *Analytical Biochem.*, 110:1-8.

Hansen, B. S., Vaughan, M. H. and Wang, L. J. (1972) *J. Biol. Chem* 247:3854.

Kaufman, R. J. and Sharp, P. A. (1982) *J. Mol. Biol.*, 159:601.

McKnight, S. L. and Gavis, E. R. (1980a) *Nucl. Acids Res.* 8, 5931-5948.

McKnight, S. L. (1980b) *Nucl. Acids Res.* 8, 5949-5964.

Mulligan, R. C. and Berg, P. (1985) *Science* 209:1422.

Southern, P. J. and Berg, P. (1982) *J. Mol. Appl. Genet.*, 1:327.

Sugden, B., Marsh, K and Yates, J. (1985) *Mol. Cell Biol.* 5:410.

Wagner, M. J., Sharp, J. A. and Summers, W. C. (1981) *Proc Natl. Acad. Sci.* USA 78, 1441-1445.

Wigler, M. Silverstein, S., Lee, L. Pellicer, A. Cheng, T. and Axel, R. (1977) *Cell* 11:223.

Wigler, M, Sweet, R., Sim, G., Wold, B., Pellicer, A., Lacy, E., Maniatis, T., Silverstein S. and Axel, R. (1979) *Cell* 16:777.

Yates, J. L., Warren, N and Sugden, B. (1985) *Nature* (Lond) 313:812.

Yoakum, G. H. (1984) *Biotechniques* 1/2:24.

What is claimed is:

1. A method for selecting for mammalian cells containing a vector comprising, providing a vector carrying and capable of expressing in said mammalian cells a gene encoding histidinol dehydrogenase, introducing the vector in a mammalian cell line such that the encoded histidinol dehydrogenase is expressed, and selecting from said cultured cells a cell that grows in the absence of a growth-supporting, exogenous supply of histidine.

2. A method as claimed in claim 1 further comprising growing said treated cells in medium containing a precursor to histidine but not containing a growth-supporting amount of histidine.

3. A method as claimed in claim 2 further comprising growing said treated cells in medium that contains the precursor, wherein said precursor is histidine.

4. A method for selecting transfected mammalian cells comprising, growing said mammalian cells transfected with a vector containing a gene encoding histidinol dehydrogenase, the histidinol dehydrogenase capable of effecting a precursor to be converted ultimately into histidine, said growing carried out in a medium supplemented with said precursor to histidine, but not in the presence of an exogenous supply of histidine sufficient to support growth.

5. A preparation for use with mammalian cells comprising, constituents present in relative amounts sufficient to support the growth of said mammalian cells, except that said preparation does not contain a growth-supporting amount of histidine and does contain a precursor to histidine.

6. A preparation as claimed in claim 5 wherein said preparation is a solution selected from the group consisting of RPMI, MEM, DMEM and BME except that said solution contains said precursor to histidine and does not contain a growth-supporting amount of histidine.

7. A method as recited in any one of claims 1 or 4 wherein the cells are human cells.

* * * * *